US009387317B2

(12) United States Patent
Stickney et al.

(10) Patent No.: US 9,387,317 B2
(45) Date of Patent: Jul. 12, 2016

(54) EXTERNAL DEFIBRILLATOR ELECTRODE, METHOD AND SYSTEM FOR REDUCING ECG ARTIFACT

(71) Applicant: Physio-Control, Inc., Redmond, WA (US)

(72) Inventors: Ronald Eugene Stickney, Edmonds, WA (US); Joseph L Sullivan, Kirkland, WA (US); Gary Debardi, Kirkland, WA (US)

(73) Assignee: Physio-Control, Inc., Redmond, WA (US)

( * ) Notice: Subject to any disclaimer, the term of this patent is extended or adjusted under 35 U.S.C. 154(b) by 0 days.

(21) Appl. No.: 14/588,291

(22) Filed: Dec. 31, 2014

(65) Prior Publication Data

US 2015/0112177 A1    Apr. 23, 2015

Related U.S. Application Data

(63) Continuation of application No. 13/686,120, filed on Nov. 27, 2012, now Pat. No. 8,929,980.

(60) Provisional application No. 61/642,414, filed on May 3, 2012.

(51) Int. Cl.
*A61N 1/04* (2006.01)
*A61N 1/39* (2006.01)
*A61B 5/0408* (2006.01)

(52) U.S. Cl.
CPC ............ *A61N 1/0472* (2013.01); *A61B 5/0408* (2013.01); *A61N 1/046* (2013.01); *A61N 1/3925* (2013.01); *A61B 2562/063* (2013.01); *Y10T 29/49169* (2015.01)

(58) Field of Classification Search
None
See application file for complete search history.

(56) References Cited

U.S. PATENT DOCUMENTS 3,505,993 A    4/1970  Lewes et al.
4,311,152 A    1/1982  Modes et al.
(Continued)

FOREIGN PATENT DOCUMENTS

EP    0801959 A2    10/1997
EP    0923961 A1    6/1999
WO    2013056194 A1    4/2013

OTHER PUBLICATIONS

Int'l Search Report and Written Opinion, PCT/US2012/071436, mailed Apr. 10, 2013, 13 pages.
(Continued)

*Primary Examiner* — Brian T Gedeon
*Assistant Examiner* — Ankit Tejani
(74) *Attorney, Agent, or Firm* — The Juhasz Law Firm P.C.

(57) ABSTRACT

An electrode for use with an external defibrillator for a patient includes a first combination circuit including a circuit node electrically coupled to an adapter for coupling to the defibrillator. The circuit node is further coupled to a monitoring node defined by a monitoring segment of a first pad of the electrode and to a therapy node defined by a therapy segment of the first pad of the electrode. The therapy segment is electrically insulated from the monitoring segment. The first combination circuit further includes a capacitor coupled between the circuit node and the therapy node. The electrode of this disclosure hence provides additional solutions for reducing ECG artifact during the operation of the electrode.

22 Claims, 10 Drawing Sheets

DEFIBRILLATION SCENE

(56) References Cited

U.S. PATENT DOCUMENTS

| | | |
|---|---|---|
| 4,355,642 A | 10/1982 | Alferness |
| 4,955,381 A | 9/1990 | Way et al. |
| 5,080,099 A | 1/1992 | Way et al. |
| 5,305,746 A | 4/1994 | Fendrock |
| 5,309,909 A | 5/1994 | Gadsby et al. |
| 5,615,295 A | 3/1997 | Yoshida et al. |
| 6,148,233 A | 11/2000 | Owen et al. |
| 6,370,428 B1 | 4/2002 | Snyder et al. |
| 6,658,291 B2 | 12/2003 | Snyder |
| 6,690,959 B2 | 2/2004 | Thompson |
| 7,006,865 B1 | 2/2006 | Cohen et al. |
| 7,092,750 B2 | 8/2006 | Van Ess |
| RE40,471 E | 8/2008 | Groenke et al. |
| 7,486,990 B2 | 2/2009 | Sullivan |
| 8,040,246 B2 | 10/2011 | Graves et al. |
| 8,054,177 B2 | 11/2011 | Graves et al. |
| 8,154,246 B1 | 4/2012 | Heitman |
| 8,615,295 B2 | 12/2013 | Savage et al. |
| 8,781,576 B2 | 7/2014 | Savage et al. |
| 2001/0041920 A1 | 11/2001 | Starkweather et al. |
| 2002/0028991 A1 | 3/2002 | Thompson |
| 2003/0097160 A1 | 5/2003 | Caby et al. |
| 2003/0167074 A1 | 9/2003 | Merry |
| 2005/0131465 A1 | 6/2005 | Freeman et al. |
| 2006/0149321 A1 | 7/2006 | Merry et al. |
| 2006/0149323 A1 | 7/2006 | Merry et al. |
| 2006/0173498 A1 | 8/2006 | Banville |
| 2009/0138057 A1 | 5/2009 | Sullivan |
| 2009/0264948 A1 | 10/2009 | Tamura et al. |
| 2009/0295326 A1 | 12/2009 | Daynes et al. |
| 2010/0114236 A1 | 5/2010 | Jiang et al. |
| 2011/0022105 A9 | 1/2011 | Owen et al. |
| 2011/0208259 A1 | 8/2011 | Pearce et al. |
| 2012/0271137 A1 | 10/2012 | Kieval |
| 2012/0310315 A1 | 12/2012 | Savage et al. |
| 2013/0096649 A1 | 4/2013 | Martin et al. |
| 2014/0213875 A1 | 7/2014 | Freeman et al. |

OTHER PUBLICATIONS

Int'l Search Report and Written Opinion, PCT/US2012/071448, mailed Feb. 8, 2013, 11 pages.

Int'l Search Report and Written Opinion, PCT/US2012/071450, mailed May 24, 2013, 10 pages.

Int'l Search Report and Written Opinion, PCT/US2012/071461, mailed Apr. 10, 2013, 14 pages.

DEFIBRILLATION SCENE

TWO MAIN TYPES OF
EXTERNAL DEFIBRILLATORS

EXTERNAL DEFIBRILLATOR ELECTRODE, METHOD AND SYSTEM FOR REDUCING ECG ARTIFACT

RELATED APPLICATIONS

This application is a continuation of U.S. patent application Ser. No. 13/686,120, filed Nov. 27, 2012, now U.S. Pat. No. 8,929,980; U.S. patent application Ser. No. 13/686,120 is a non-provisional of U.S. provisional application 61/642,414, filed May 3, 2012; both of these applications are incorporated by reference in their entirety.

FIELD

This invention generally relates to external defibrillators.

BACKGROUND

In humans, the heart beats to sustain life. In normal operation, it pumps blood through the various parts of the body. More particularly, the various chamber of the heart contract and expand in a periodic and coordinated fashion, which causes the blood to be pumped regularly. More specifically, the right atrium sends deoxygenated blood into the right ventricle. The right ventricle pumps the blood to the lungs, where it becomes oxygenated, and from where it returns to the left atrium. The left atrium pumps the oxygenated blood to the left ventricle. The left ventricle, then, expels the blood, forcing it to circulate to the various parts of the body and from where it returns to the right atrium to start the oxygenation-deoxygenation cycle of the blood all over again.

The heart chambers pump because of the heart's electrical control system. More particularly, the sinoatrial (SA) node generates an electrical impulse, which generates further electrical signals. These further signals cause the above-described contractions of the various chambers in the heart to occur in the correct sequence. The electrical pattern created by the sinoatrial (SA) node is called a sinus rhythm.

Sometimes, however, the electrical control system of the heart malfunctions, which can cause the heart to beat irregularly, or not at all. The cardiac rhythm is then generally called an arrhythmia. Arrhythmias may be caused by electrical activity from locations in the heart other than the SA node. Some types of arrhythmia may result in inadequate blood flow, thus reducing the amount of blood pumped to the various parts of the body. Some arrhythmias may even result in a Sudden Cardiac Arrest (SCA). In an SCA, the heart fails to pump blood effectively, and, if not corrected, can result in death. It is estimated that SCA results in more than 250,000 deaths per year in the United States alone. Further, an SCA may result from a condition other than an arrhythmia.

One type of arrhythmia associated with SCA is known as Ventricular Fibrillation (VF). VF is a type of malfunction where the ventricles make rapid, uncoordinated movements, instead of the normal contractions. When that happens, the heart does not pump enough blood to deliver enough oxygen to the vital organs. The person's condition will deteriorate rapidly and, if not corrected in time, will result in death, e.g. within ten minutes.

Ventricular Fibrillation can often be reversed using a lifesaving device called a defibrillator. A defibrillator, if applied properly, can administer an electrical shock to the heart. The shock may terminate the VF, thus giving the heart the opportunity to resume normal contractions in pumping blood. If VF is not terminated, the shock may be repeated, often at escalating energies.

A challenge with defibrillation is that the electrical shock must be administered very soon after the onset of VF. There is not much time to do this since the survival rate of persons suffering from VF decreases by about 10% for each minute the administration of a defibrillation shock is delayed. After about 10 minutes the rate of survival for SCA victims averages less than 2%.

The challenge of defibrillating early after the onset of VF is being met in a number of ways. First, for some people who are considered to be at a higher risk of VF or other heart arrythmias, an Implantable Cardioverter Defibrillator (ICD) can be implanted surgically. An ICD can monitor the person's heart, and administer an electrical shock as needed. As such, an ICD reduces the need to have the higher-risk person be monitored constantly by medical personnel.

Regardless, VF can occur unpredictably, even to a person who is not considered at risk. As such, VF can be experienced by many people who lack the benefit of ICD therapy. When VF occurs to a person who does not have an ICD, they collapse, because the blood flow has stopped. They should receive therapy quickly after the onset of VF or they will die.

For a VF victim without an ICD, a different type of defibrillator can be used, which is called an external defibrillator. External defibrillators have been made portable, so they can be brought to a potential VF victim quickly enough to revive them.

During VF, the person's condition deteriorates because the blood is not flowing to the brain, heart, lungs, and other organs. The blood flow must be restored, if resuscitation attempts are to be successful.

Cardiopulmonary Resuscitation (CPR) is one method of forcing blood to again flow in a person experiencing cardiac arrest. In addition, CPR is the primary recommended treatment for some patients with some kinds of non-VF cardiac arrest, such as asystole and pulseless electrical activity (PEA). CPR is a combination of techniques that include chest compressions to force blood circulation, and rescue breathing to force respiration.

Properly administered CPR provides oxygenated blood to critical organs of a person in cardiac arrest, thereby minimizing the deterioration that would otherwise occur. As such, CPR can be beneficial for persons experiencing VF, because it slows down the deterioration that would otherwise occur while a defibrillator is being retrieved. For patients with an extended down-time, survival rates are higher if CPR is administered prior to defibrillation.

One common challenge for both automated and manual rhythm assessment in connection with defibrillation is that the high level of charges applied to a therapy electrode of a defibrillator for the purpose of "shocking" the heart may electrically interfere with the low level charge electrical signals that are generated by a monitoring electrode that may be used with the defibrillator for the purpose of monitoring the patient throughout the defibrillation process. Another common challenge for both automated and manual rhythm assessment is the occurrence of ECG artifacts during the resuscitation process which can adversely affect automated and manual rhythm assessment. ECG artifact may result from chest compressions, ambulance transport, or other patient motion. ECG artifact caused by patient motion can occur because when the patient's skin is stretched the voltage generated in or near the stratum granulosum can temporarily change by as much as a few millivolts. ECG artifact may also result from deformation of the electrode's metal-electrolyte interface, which can temporarily change the electrode's halfcell potential by as much as a few millivolts. ECG artifact may also result from movement of electrostatically charged rescuers near the patient or the defibrillator even when the patient is not touched. Electrostatically induced artifact occurs when a moving, electrostatically charged rescuer induces current flow through the ECG signal path. When the currents flow through the stratum corneum (top layer of the skin, which consists of dead skin cells) under each electrode, a differential voltage (sometimes exceeding twenty millivolts) can be generated at the input to the ECG amplifier.

While advanced medical device solutions exist for reducing electrical interference of ECG monitoring signals by the high level defibrillator charges and ECG artifact, defibrillator operators may benefit from improved electrical and ECG artifact solutions.

BRIEF SUMMARY

The present description gives instances of devices, systems, software and methods, the use of which may help overcome problems and limitations of the prior art.

An electrode for use with an external defibrillator for a patient includes a first combination circuit including a circuit node electrically coupled to an adapter for coupling to the defibrillator. The circuit node is further coupled to a monitoring node defined by a monitoring segment of a first pad of the electrode and to a therapy node defined by a therapy segment of the first pad of the electrode. The therapy segment is electrically insulated from the monitoring segment. The coupling to the therapy node includes a capacitor.

A defibrillator system includes a defibrillator and an electrode assembly for use with an external defibrillator for a patient. The defibrillator includes an energy storage device for storing an electrical charge, a defibrillation and monitoring port, a defibrillator processor configured to control use of ECG signals from a patient and when an electrical charge is applied through the defibrillation and monitoring port of the defibrillator to the patient. The electrode includes a first pad, an adapter, and a first combination circuit. The first pad includes a monitoring segment for receiving the ECG signals of the patient and defines a monitoring node. The first pad further includes a therapy segment for delivering the charge to the patient from the defibrillator. The therapy segment is electrically insulated from the monitoring segment and the therapy segment defines a therapy node. The adapter is configured for coupling to the defibrillator. The first combination circuit includes a circuit node electrically coupled to the adapter. The circuit node is further coupled to the monitoring node and to the therapy node. The coupling to the therapy node includes a capacitor.

A method for monitoring and delivering a charge to a patient by an external defibrillator includes the steps of: apply a therapy segment and a monitoring segment to a patient; define a single communication channel for transmission of both the signal of an ECG of the patient from the monitoring segment and the charge of the defibrillator to the therapy segment for delivery to the patient; connect the therapy segment and the monitoring segment to a defibrillator through the single communication channel; monitor the ECG signal of the patient from the monitoring segment over the single communication channel; and deliver a charge from the defibrillator to the patient through the therapy segment over the single communication channel.

These and other features and advantages of this description will become more readily apparent from the following Detailed Description, which proceeds with reference to the drawings, in which:

BRIEF DESCRIPTION OF THE DRAWINGS

FIG. 1 is an illustrative diagram of a scene showing the use of an external defibrillator to provide emergency cardiac patient care, with which this disclosure may be used.

FIG. 2 is a table listing two illustrative types of the external defibrillator shown in FIG. 1, and who they might be used by.

DETAILED DESCRIPTION

Figures 1, 2:
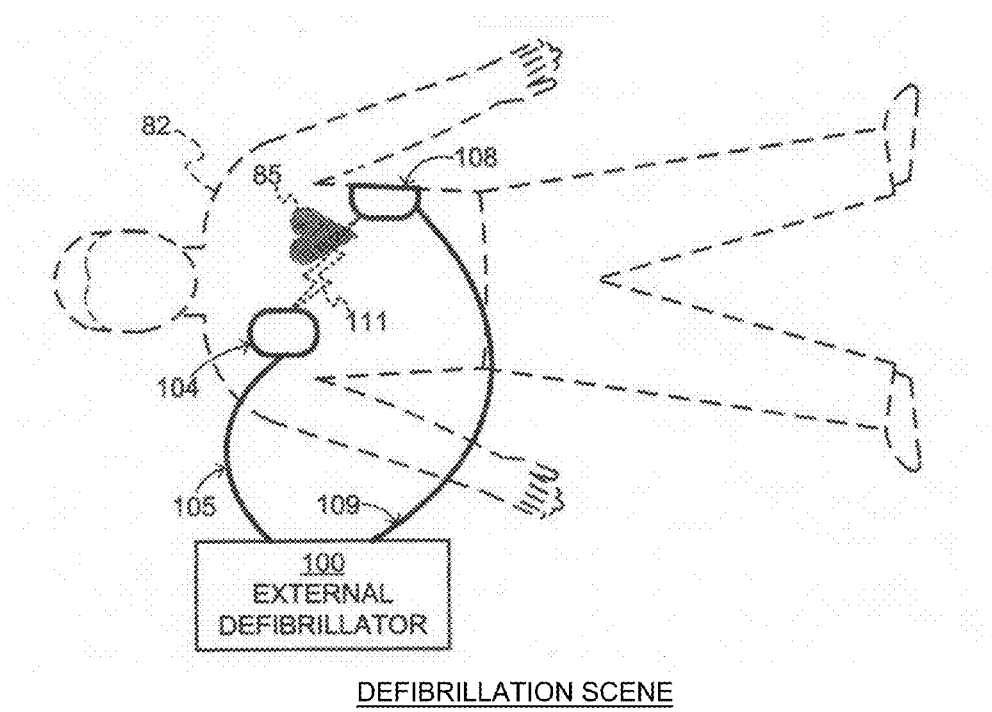

FIG. 1 is a diagram of a defibrillation scene showing the use of an external defibrillator to save the life of a person according to this disclosure. As shown, a person 82 is lying on his back. Person 82 could be a patient in a hospital, or someone found unconscious, and then turned over onto his back. Person 82 is experiencing a condition in their heart 85, which could be Ventricular Fibrillation (VF).

A portable external defibrillator 100 has been brought close to person 82. At least two defibrillation electrodes 104, 108 are typically provided with external defibrillator 100, and are sometimes called electrodes 104, 108. Electrodes 104, 108 are coupled together with external defibrillator 100 via respective electrode leads 105, 109. A rescuer (not shown) has attached electrodes 104, 108 to the skin of person 82. Defibrillator 100 is administering, via electrodes 104, 108, a brief, strong electric pulse 111 through the body of person 82. Pulse 111, also known as a defibrillation shock, also goes through heart 85, in an attempt to restart it, for saving the life of person 82.

Defibrillator 100 can be one of different types, each with different sets of features and capabilities. The set of capabilities of defibrillator 100 is determined based upon who would use it and what training they would be likely to have. Examples are now described.

FIG. 2 is a table listing two typical types of external defibrillators, and who they are primarily intended to be used by. A first type of defibrillator 100 is generally called a defibrillator-monitor, because the defibrillator part is typically formed as a single unit with a patient monitor part. A defibrillator-monitor is sometimes called monitor-defibrillator. A defibrillator-monitor is intended to be used by persons in the medical profession, such as doctors, nurses, paramedics, emergency medical technicians, etc. who may be trained to provide medical treatment to the patient during a defibrillation process based upon information provided by the monitor. Such a defibrillator-monitor is intended to be used in a pre-hospital or hospital scenario.

The defibrillator part may be dedicated to a particular mode of operation. Alternatively, the defibrillator part may be configured to operate in more than one mode of operation. One mode of operation of the defibrillator part may be that of an automated defibrillator, which can determine whether a shock is needed and, if so, charge to a predetermined energy level and instruct the user to administer the shock. Another mode of operation may be that of a manual defibrillator, where the user determines the need and controls administering the shock. In this embodiment, one illustrative defibrillator is configured to enable both automated defibrillation and manual defibrillation modes of operation depending upon the selection of the user. As a patient monitor, the device has features additional to what is minimally needed for mere operation as a defibrillator. These features can be for monitoring physiological indicators of a person in an emergency scenario. These physiological indicators are typically monitored as signals. For example, these signals can include a person's full ECG (electrocardiogram) signals, or impedance between two electrodes. Additionally, these signals can be about the person's temperature, non-invasive blood pressure (NIBP), arterial oxygen saturation/pulse oximetry (SpO2), the concentration or partial pressure of carbon dioxide in the respiratory gases, which is also known as capnography, and so on. These signals can be further stored and/or transmitted as patient data.

A second type of external defibrillator 100 is generally called an AED, which stands for "Automated External Defibrillator". An AED typically makes the shock/no shock determination by itself, automatically. Indeed, it can sense enough physiological conditions of the person 82 via only the shown defibrillation electrodes 104, 108 of FIG. 1. In its present embodiments, an AED can either administer the shock automatically, or instruct the user to do so, e.g. by pushing a button. Being of a much simpler construction, an AED typically costs much less than a defibrillator-monitor. As such, it makes sense for a hospital, for example, to deploy AEDs at its various floors, in case the more expensive defibrillator-monitor is more critically being deployed at an Intensive Care Unit, and so on.

AEDs, however, can also be used by people who are not trained in the medical profession. More particularly, an AED can be used by many professional first responders, such as policemen, firemen, etc. Even a person with only first-aid training can use one. And AEDs increasingly can supply instructions to whoever is using them.

AEDs are thus particularly useful, because it is so critical to respond quickly, when a person suffers from VF. Often, the people who will first reach the VF sufferer may not be in the medical profession.

Increasing awareness of the short survival time of a patient experiencing VF, has resulted in AEDs being deployed more pervasively in public or semi-public spaces, enabling members of the public to use one provided they have obtained first aid and CPR/AED training. In this way, defibrillation can be administered sooner after the onset of VF, to hopefully be effective in rescuing the person.

There are additional types of external defibrillators, which are not listed in FIG. 2. For example, a hybrid defibrillator can have aspects of an AED, and also of a defibrillator-monitor. An illustrative example may be an AED provided with an ECG monitoring capability.

Figure 3:
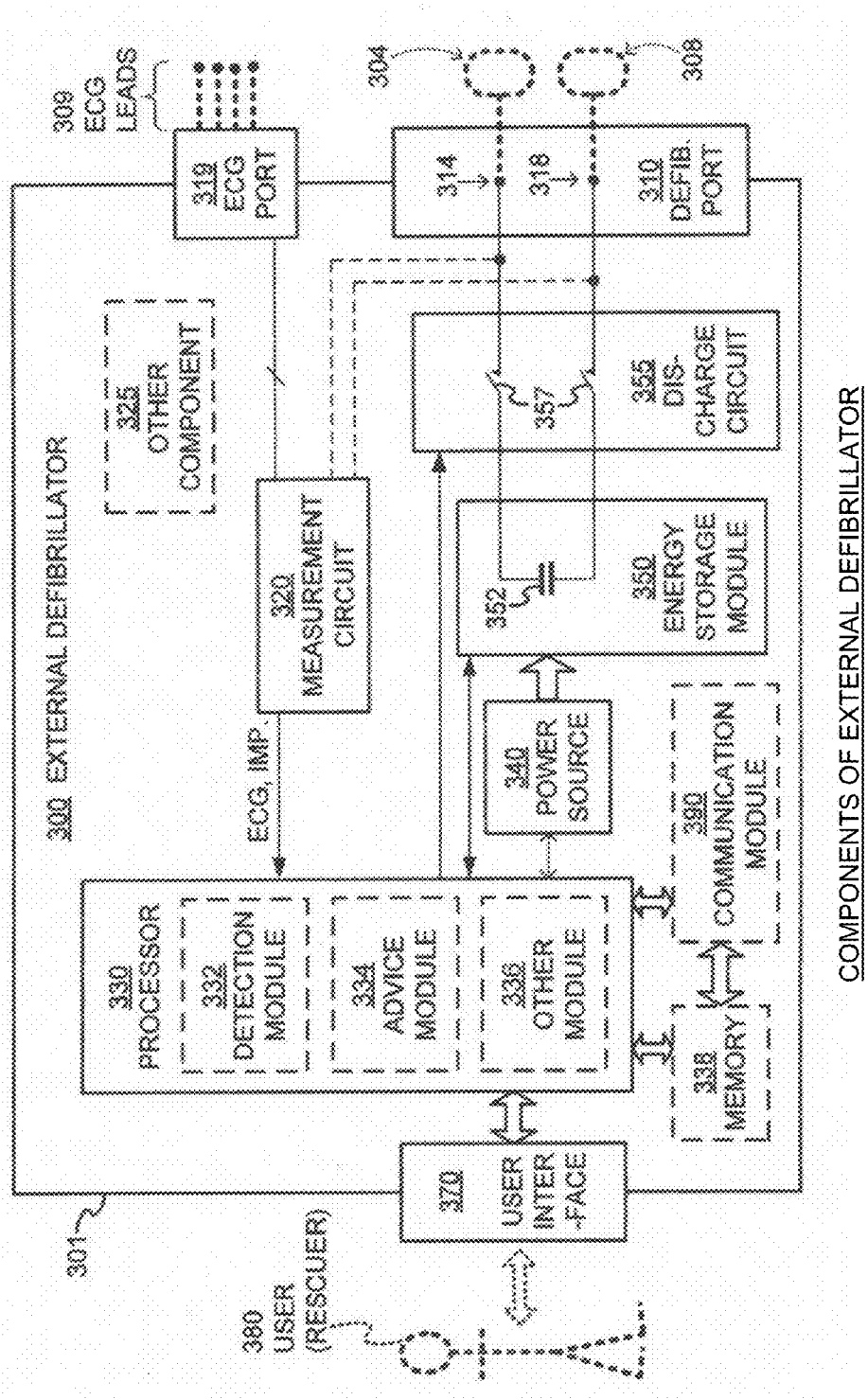
FIG. 3 is a diagram showing components of an external defibrillator, such as the one shown in FIG. 1, configured in an illustrative embodiment.

FIG. 3 is a diagram showing components of an external defibrillator 300 configured in an illustrative embodiment according to this disclosure. These components can be configured, for example, in external defibrillator 100 of FIG. 1. Plus, these components of FIG. 3 can be provided in a housing 301, which is also known as casing 301.

External defibrillator 300 is intended for use by a user 380, who would be the rescuer. Defibrillator 300 typically includes a defibrillation port 310, which may be configured as a socket (not shown) in housing 301. Defibrillation port 310 includes nodes 314, 318. Defibrillation electrodes 304, 308, which can be similar to electrodes 104, 108 in FIG. 1, can be plugged into defibrillation port 310, so as to make electrical contact with nodes 314, 318, respectively. It is also possible that electrodes can be hard-wired to defibrillation port 310, etc. Either way, defibrillation port 310 can be used for guiding to person 82 via electrodes an electrical charge that has been stored in defibrillator 300, as discussed below.

If defibrillator 300 is actually a defibrillator-monitor, as was described with reference to FIG. 2, then it will typically also have an ECG port 319 in housing 301, for plugging in ECG leads 309. ECG leads 309 can help sense an ECG signal, e.g. a 12-lead signal, or a signal taken from a different number of leads. Moreover, a defibrillator-monitor could have additional ports (not shown), and another component 325 for the above described additional features, such as for receipt of patient signals.

Defibrillator 300 also includes a measurement circuit 320. Measurement circuit 320 receives physiological signals from ECG port 319, and also from other ports, if provided. These physiological signals are sensed, and information about them is rendered by circuit 320 as data, or other signals, etc.

If defibrillator 300 is actually an AED, it may lack ECG port 319. Measurement circuit 320 can obtain physiological signals in this case through nodes 314, 318 instead, when defibrillation electrodes 304, 308 are attached to person 82. In these cases, a person's ECG signal can be sensed as a voltage difference between electrodes 304, 308. Plus, impedance between electrodes 304, 308 can be sensed for detecting, among other things, whether these electrodes 304, 308 have been inadvertently disconnected from the person.

Defibrillator 300 also includes a processor 330. Processor 330 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Processor 330 may include a number of modules. One such module can be a detection module 332, which senses outputs of measurement circuit 320. Detection module 332 can include a VF detector. Thus, the person's sensed ECG can be used to determine whether the person is experiencing VF.

Another such module in processor 330 can be an advice module 334, which arrives at a piece of instructional advice based on outputs of detection module 332. Advice module 334 can include a Shock Advisory Algorithm residing in a memory unit (not shown) in the advice module for instructing the processor to implement decision rules, etc. Alternatively, the Shock Advisory Algorithm may reside in part or in whole on a memory 338 of the defibrillator. The instruction to the processor can be to shock, to not shock, to administer other forms of therapy, and so on. If the instruction to the processor is to shock, in some external defibrillator embodiments, the processor is configured to report that instruction to the user via user interface 370, and to prompt the user to do it. In other embodiments, the processor may be configured to execute the instructional advice, by administering the shock. If the instructional advice is to administer CPR, the processor may be configured to enable defibrillator 300 to issue prompts to administer CPR, etc.

Processor 330 can include additional modules, such as module 336, for other functions. In addition, if other component 325 is provided, it may be operated in part by processor 330 or by another processor.

Defibrillator 300 optionally further includes the memory 338, which can work together with processor 330. Memory 338 may be implemented in any number of ways. Such ways include, by way of example and not of limitation, nonvolatile memories (NVM), read-only memories (ROM), random access memories (RAM), any combination of these, etc.. Memory 338, if provided, may include programs containing instructions for execution by processor 330 or other processors that may be included in the external defibrillator. The programs provide instructions for execution by the processor 330, and can also include instructions regarding protocols and decision making analytics, etc. that can be used by advice module 334. In addition, memory 338 can store prompts for user 380, etc. Moreover, memory 338 can store patient data.

Defibrillator 300 may also include a power source 340. To enable portability of defibrillator 300, power source 340 typically includes a battery. Such a battery is typically implemented as a battery pack, which can be rechargeable or not. Sometimes, a combination is used, of rechargeable and non-rechargeable battery packs. Other embodiments of power source 340 can include an AC power override, whereby AC power, instead of power from power source 340 is delivered to an energy storage module 350 when AC power is available. In some embodiments, power source 340 is controlled by processor 330.

Defibrillator 300 additionally includes the energy storage module 350. Module 350 is where electrical energy is stored in preparation for a sudden discharge to administer a shock. The charge to module 350 from power source 340 to the right amount of energy can be controlled by processor 330. In typical implementations, module 350 includes one or more capacitors 352, and may include other circuitry.

Defibrillator 300 moreover includes a discharge circuit 355. Circuit 355 can be controlled to permit the energy stored in module 350 to be discharged to nodes 314, 318, and thus also to defibrillation electrodes 304, 308. Circuit 355 can include one or more switches 357. Those can be made in a number of ways, such as by an H-bridge, and in other ways well known in the art.

Defibrillator 300 further includes the user interface 370 for user 380. User interface 370 can be made in any number of ways. For example, interface 370 may include a screen, to display a parameter of a patient that is detected and measured, provide visual feedback to the rescuer for their resuscitation attempts, and so on. Interface 370 may also include a speaker, to issue voice prompts, etc. Interface 370 may additionally include various controls, such as pushbuttons, keyboards, and so on. In addition, discharge circuit 355 can be controlled by processor 330, or directly by user 380 via user interface 370, and so on.

Defibrillator 300 can optionally include other components. For example, a communication module 390 may be provided for communicating with other devices. Such communication can be performed wirelessly, or via wire, or by infrared communication, and so on. In this way, data can be communicated from the defibrillator 300 to external devices, such as patient data, incident information, therapy attempted, CPR performance, and so on.

Figure 4:
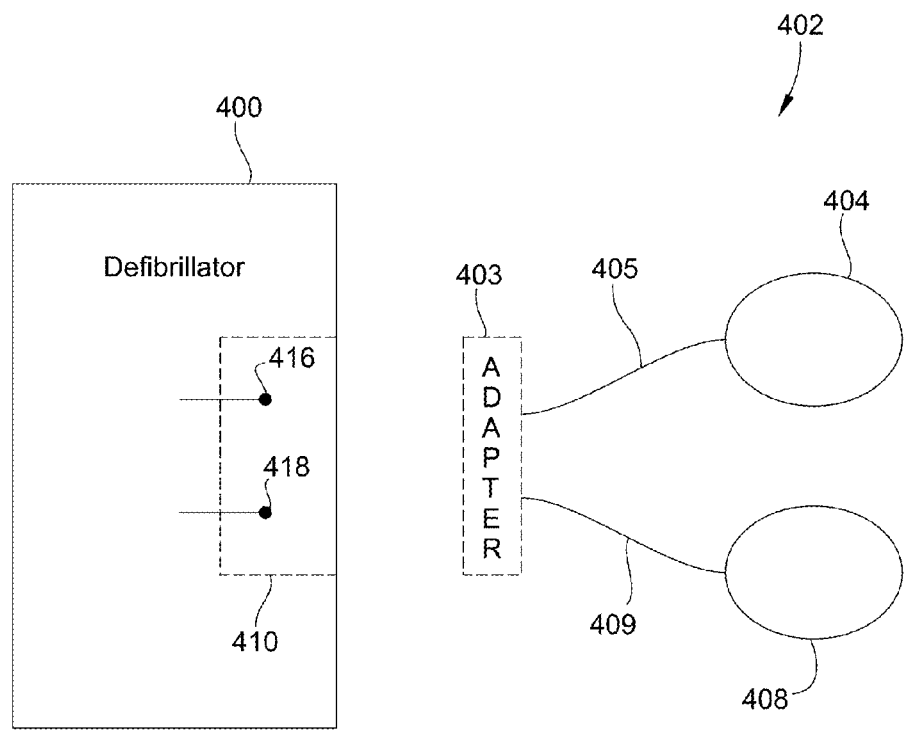
FIG. 4 illustrates a prior art electrode with adapter for connecting to a defibrillator.

FIG. 4 illustrates a prior art electrode 402 with adapter 403 for connecting to a defibrillator 400. Defibrillator 400 comprises an energy storage device (350 in FIG. 3) for storing an electrical charge; a defibrillation and monitoring port 410 (also shown as 310, 319 in FIG. 3); a defibrillator processor (330 in FIG. 3), and a memory (338 in FIG. 3). The defibrillation and monitoring port 410 includes a defibrillator electrode connect port 416 (310 in FIG. 3) and a monitoring electrode connect port 418 (319 in FIG. 3) and the processor is configured to control when an electrical charge is applied to the defibrillation port 416 for defibrillating a patient and to control the ECG signal that is being received from the patient through the monitoring electrode connect port 418. Defibrillator 410, and its various components, can be as already described with reference to FIG. 3 above. Electrode 402 comprises pads 404, 408 which form two half cells of electrode 402, each having leads 405, 409, respectively, which provide an electrical path for the travel of electrical signals in the form of the electrical charge from the defibrillation port 416 to the pads 404, 408 for defibrillating a patient and the ECG signal from the pads 404, 408 to the defibrillator 400 for monitoring the patient ECG. Adapter 403 is a device that is configured to route the electrical signals traveling between the defibrillator 400 and the pads 404, 408. In addition, the adapter 403 may also be configured to route a high frequency, low voltage signal generated by the defibrillator (used for measuring the impedance between the electrode pads 404 and 408) for application to the pads 404 and 408.

Figure 5:
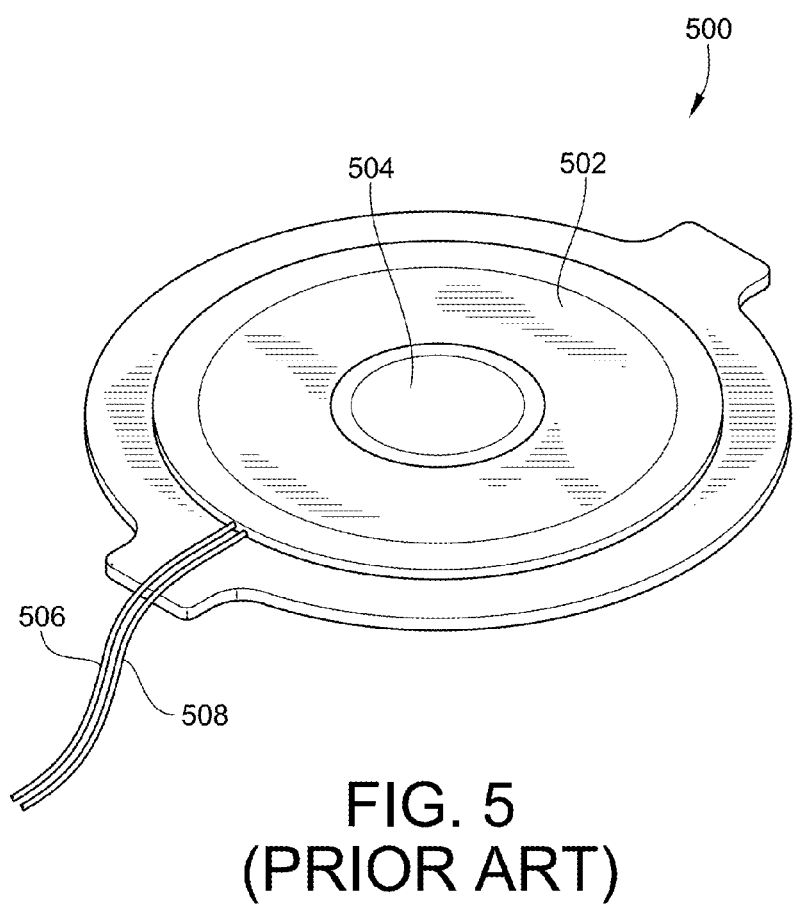
FIG. 5 is a perspective view of a prior art electrode utilizing dedicated wire leads for each of the therapy element and the monitoring element that make up the electrode.

FIG. 5 is a perspective view of a prior art electrode 500 utilizing dedicated wire leads 506, 508 for each of a therapy element 502 and a monitoring element 504 that make up the electrode. The prior art electrode 500 shown in FIG. 5 actually forms one of pads 404, 408 shown in FIG. 4, that is to say, one of the half cells required for operation of the electrode 402 in FIG. 4. Another half cell, or prior art electrode 500 would be required to complete the electrode 402 of FIG. 4. The processor of the defibrillator with which the prior art electrode 500 is used is configured to control when an electrical charge is applied to the therapy segment 502 for defibrillating a patient and to process the ECG signal that is being received from the patient through the monitoring segment 504, as described in FIG. 4.

Having thus introduced background on the general operation of prior art defibrillator and electrode system, we now turn to features that are provided by this disclosure.

Figure 6:
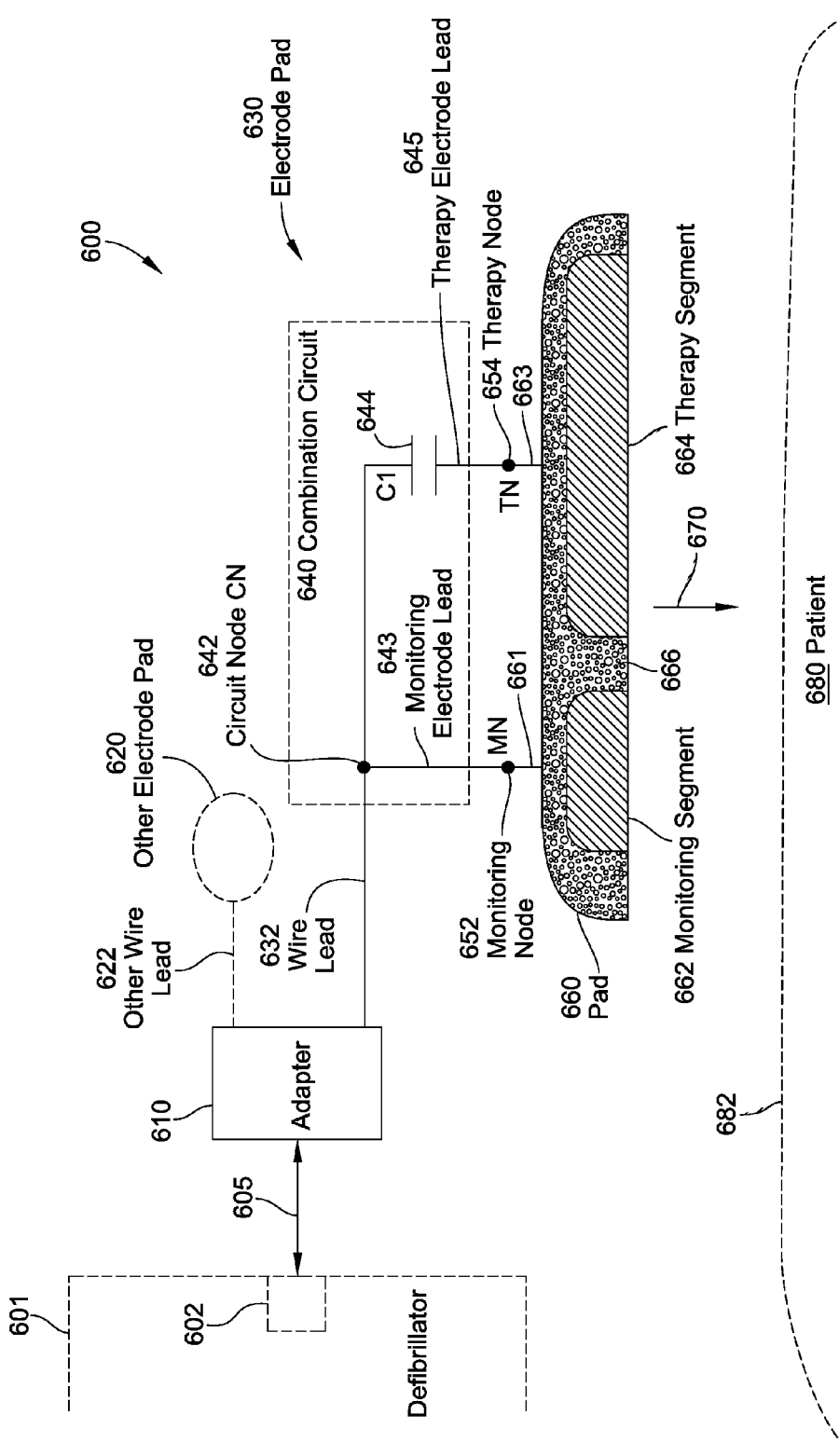
FIG. 6 is an illustrative electrode for use in monitoring a patient and delivering a charge to a patient in connection with a cardiac arrhythmia according to this disclosure.

FIG. 6 is an illustrative electrode or electrode pad 630 for use in monitoring a patient 680 and delivering a charge to the patient in connection with a cardiac arrhythmia according to this disclosure. FIG. 6 also shows the electrode 630 in combination with another electrode or electrode pad 620 in an electrode system 600. The other electrode pad 620 which includes a wire lead 622 is configured and operates in like manner to the configuration and operation of the electrode 630 as will now be described.

Electrode 630 comprises a first pad 660, an adapter 610, and a first combination circuit 640. It will be appreciated that the configuration and operation of adapter 610 is in this illustrative embodiment described as it pertains to electrode 630 but adapter 610 may provide a like configuration and operation with respect to the other electrode pad 620 of the electrode system 600 shown in FIG. 6. The first pad 660 illustratively includes a monitoring segment 662 for receiving an ECG of the patient 680 and defines a monitoring node 652. The first pad further includes a therapy segment 664 for delivering a charge to the patient 680 from a defibrillator 601. The therapy segment may also be used by the defibrillator to monitor the impedance of the patient. The therapy segment 664 is electrically insulated from the monitoring segment 662 by an insulator 666. The therapy segment 664 additionally defines a therapy node 654. The adapter 610 couples the electrode 630 to the defibrillator 601. Adapter 610 is an electronic device that, as applied to the disclosure of the electrode 630 of this disclosure, is configured to route the electrical signals traveling between the defibrillator 601 and the electrode pad 630. More specifically, the adapter is configured to route ECG signals from the monitoring segment 662 of the electrode 630 for use by the defibrillator 601 and to route a charge generated by the defibrillator 601 for application to the therapy segment 664. In addition, the adapter 610 may also be configured to route a high frequency, low voltage signal generated by the defibrillator 601 (used for measuring the impedance between the electrode pads 620 and 630) for application to the therapy segment 664. As previously indicated, the adapter may be configured to provide a like function for the other electrode pad 620 that may form the electrode system 600.

The first combination circuit 640 includes a circuit node 642 electrically coupled to the adapter 610. The circuit node 642 is additionally coupled to the monitoring node 652 and to the therapy node 654. The coupling to the therapy node includes a capacitor 644.

More specifically, the monitoring segment 662 may illustratively be connected (such as by a monitoring segment lead 661) to a first end of a monitoring electrode lead 643 with the point of connection of the monitoring segment to the first end of the monitoring electrode lead 643 defining the monitoring node 652. In addition, the monitoring electrode lead 643 may illustratively be connected at a second end to a first end of the wire lead 632, with the point of connection of the monitoring segment lead to the wire lead defining the circuit node 642. The wire lead 632 is coupled at a second end to the adapter 610 in this example.

In addition, the therapy segment 664 may illustratively be connected (such as by a therapy segment lead 663) to a first end of a therapy electrode lead 645, the point of connection of the therapy segment 664 to the first end of the therapy electrode lead 645 defining the therapy node 654. The therapy electrode lead 645 is connected at a second end to a second end of the capacitor 644 in this example, the first end of the capacitor 644 being coupled to the circuit node 642. Advantageously, the capacitor 644 is selected to also allow for the high frequency, low voltage signal generated by the defibrillator 601 for measuring impedance to be passed to the therapy node 654 while allowing the charge from the defibrillator to pass to the therapy node for application through the therapy segment to the patient.

The first combination circuit 640 is electrically coupled to the adapter 610 by the wire lead 632 and as previously indicated the adapter is electrically coupled to the defibrillator 601. Specifically, an electrical signal path 605 may be provided between the adapter 610 and the defibrillator 601 for this purpose, which may illustratively be a wired lead. Alternatively, the electrical signal path 605 may be a wireless connection or a combination wired and wireless connection. For example, a wired connection may be used for delivery of the defibrillator charge to the patient while a wireless connection may be used to pass the ECG signals from the patient to the defibrillator. The adapter is coupled to the defibrillator at a defibrillation and monitoring port 602 which includes a defibrillator electrode connect port (shown as 416 in FIG. 4) and a monitoring electrode connect port (shown as 418 in FIG. 4) which operate in a manner previously described in connection with FIG. 4.

The defibrillator 601 comprises a defibrillator processor (330 in FIG. 3) configured to control use of the ECG signals from the monitoring segment by the defibrillator 601 and when an electrical charge is applied to the defibrillation electrode connect port (shown as 416 in FIG. 4) of the defibrillation and monitoring port 602 of the defibrillator 601 for defibrillating the patient 680. The defibrillator 601 further includes a memory unit (338 in FIG. 3) including instructions for the defibrillator processor to execute for the control of the use of the ECG signals from the monitoring segment 662 by the defibrillator 601 and when the electrical charge is applied to the defibrillation electrode connect port (shown as 416 in FIG. 4) of the defibrillation and monitoring port 602 of the defibrillator 601 for defibrillating the patient 680. The use of the ECG signals from the monitoring segment controlled by the defibrillator processor may be for display of the ECG signals on a display (not shown). The display on which the ECG signals from the monitoring segment 662 are displayed by the defibrillator processor may be a display (not shown) on the defibrillator. Alternatively, the use of the ECG signals from the monitoring segment 662 controlled by the defibrillator processor may be for print-out of the ECG signals on a printer (not shown) that is either a part of the defibrillator 601 or electrically connected to the defibrillator 601 by hard wire or wirelessly.

In operation, the electrode pad 630 is applied to the patient 680 such that the monitoring segment 662 and the therapy segment 664 illustratively lie against the skin 682 of the patient. The point at which the monitoring segment 662 and the therapy segment 664 lie against the skin 682 defines an interface 670 between these segments and the skin as shown in FIG. 6.

As previously described, the processor of defibrillator 601 is configured to control when an electrical charge is applied to the defibrillation electrode connect port (shown as 416 in FIG. 4) of the defibrillation and monitoring port 602 of the defibrillator 601 for defibrillating the patient 680 and to control the ECG signal that is being received from the patient at the monitoring electrode connect port (shown as 418 in FIG. 4). More specifically, the electrical charge applied by the processor to the defibrillator electrode connect port travels signal path 605 and is applied to adapter 610 which routes the charge signal to the therapy segment 664. The routed charge travels wire lead 632 through circuit note 642 to capacitor 644 and passes the charge signal through therapy electrode lead 645 through therapy node 654 to the therapy segment 664 where it is applied across interface 670 and the skin 682 to the patient. In this way the therapy segment 664 of the electrode pad 630 provides a half circuit for the application of a charge to the patient. A therapy segment (not shown) in the other electrode pad 620 shown in FIG. 6 provides the other half circuit which together with the electrode pad 630 completes the circuit for the application of the defibrillation charge to the patient.

Contemporaneously, ECG signals that are detected by the monitoring segment 662 are passed by monitoring node 652 along monitoring electrode lead 643 through circuit node 642 along wire lead 632 where the signal is applied to the adapter 610. The adapter couples the ECG signal to the defibrillator. The adapter applies the ECG signal over signal path 605 to the monitoring electrode connect port of the defibrillation and monitoring port 602 where the defibrillator processor processes the ECG signal for use by the defibrillator. A monitoring segment (not shown) in the other electrode pad 620 shown in FIG. 6 provides the other half circuit which together with the electrode pad 630 completes the circuit for the detection of the ECG by the electrode system.

Figure 7:
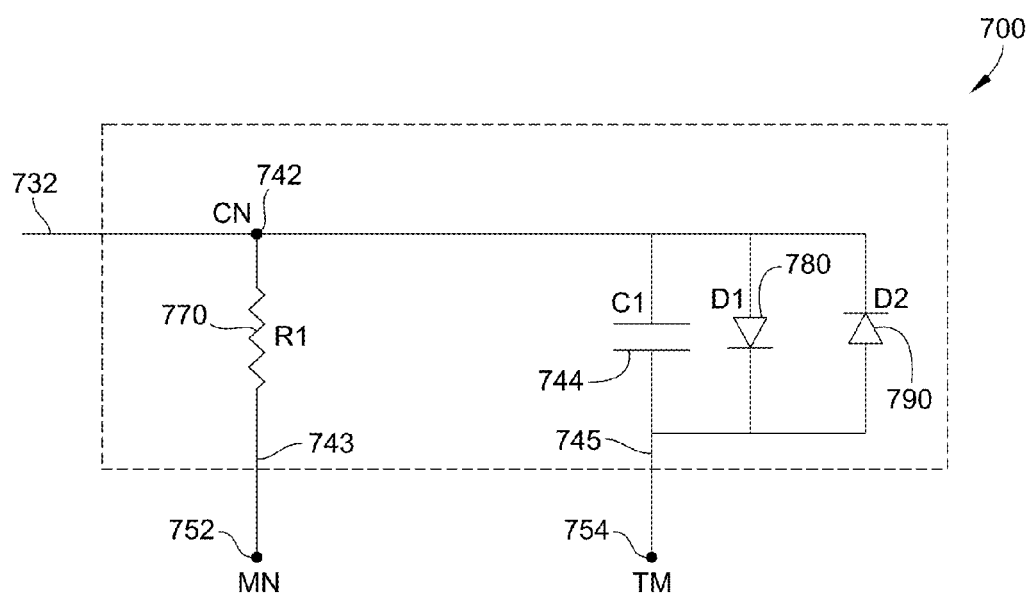
FIG. 7 is an alternative illustrative embodiment for the first combination circuit 640 for use in the electrode of FIG. 6.

FIG. 7 depicts an alternative illustrative embodiment for the first combination circuit 640 for use in the electrode 630 of FIG. 6. The first combination circuit 700 includes a circuit node 742 electrically coupled to an adapter (not shown). The circuit node 742 is additionally coupled to the monitoring node 752 and to the therapy node 754. The coupling to the therapy node includes a capacitor 744. The foregoing components and connections have been discussed in connection with the description of the first combination circuit 640 in FIG. 6 above. In addition, the capacitor 744 allows the high frequency, low voltage signal generated by the defibrillator (601 in FIG. 6) for measuring impedance to be passed to the therapy node 742. In the illustrative embodiment shown in FIG. 7, the first combination circuit (and hence the electrode or electrode pad 630 in FIG. 6 of which this FIG. 7 first combination circuit 700 forms a part of) further comprises a resistor 770 connected between the circuit node 742 and the monitoring node 752 for minimizing the current flow of the charge signal across the resister to monitoring node 752. More specifically, the resistor limits the current flow of the charge generated by the defibrillator across the resistor.

Additionally, and as shown in FIG. 7, the first combination circuit may further comprise a first diode 780 connected between the circuit node 742 and the therapy node 754 in parallel with the capacitor 744 for passing the charge generated by the defibrillator for application to the therapy segment in a forward direction. In addition, and as also shown in FIG. 7, the first combination circuit may further comprise a second diode 790 connected between the circuit node 742 and the therapy node 754 in parallel with the capacitor 744 for passing the charge generated by the defibrillator for application to the therapy segment in a reverse direction. Additionally, as also shown in FIG. 7, the first combination circuit may further include a monitoring electrode lead 743 and a therapy electrode lead 745.

As described in FIG. 6, the electrode pad 630 forms one half of an electrical circuit of the electrode system 600; the other half being formed by the other electrode pad 620. As previously described, the other electrode pad 620 may be configured in function and operation in a manner like the electrode pad 630 is configured to function and operate. In an alternative embodiment where the electrode system 600 is formed from the electrode pad 630 up, the electrode may be provided with additional components to form the electrode system 600. In this example, the electrode pad 630 of FIG. 6 may further comprise a second electrode pad shown as the other electrode pad 620 in FIG. 6 which may also include a second pad like pad 660 of electrode pad 630 for contact with the patient. The second pad may include a monitoring segment (like monitoring segment 662 of electrode pad 630) for receiving an ECG of the patient and defining a monitoring node (like monitoring node 652 of electrode pad 630) and a therapy segment (like therapy segment 664 of electrode pad 630) for delivering a charge to the patient from the defibrillator 601, which may be electrically insulated from the monitoring segment (such as with the insulator 666 of electrode pad 630). The therapy segment defines a therapy node in this example (like therapy node 654 of electrode pad 630). In addition; the second pad may include a second lead which may be the other wire lead 622 shown in FIG. 6 for coupling the second pad to the adapter 610. The second electrode pad or the other electrode pad shown in FIG. 6 may further include a second combination circuit including a circuit node electrically coupled to the adapter (like circuit node 642 of electrode pad 630). The circuit node may be coupled to the monitoring node of the second pad and to the therapy node of the second pad. The coupling to the therapy node includes a capacitor (like capacitor 644 of electrode pad 630).

Figure 8:
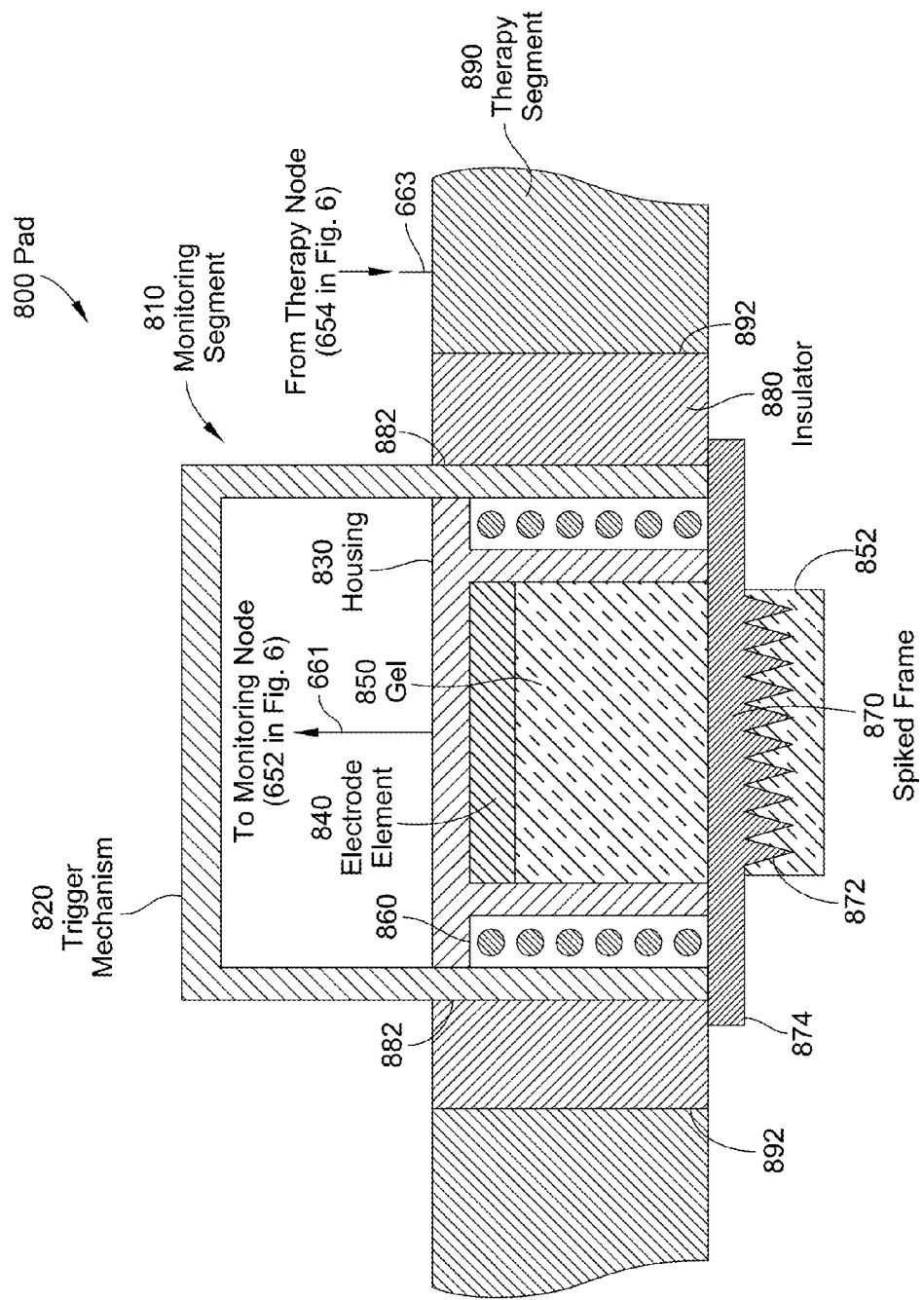
FIG. 8 is a cross-sectional view of an illustrative embodiment of the pad 660 of the electrode pad 630 of FIG. 6, shown in FIG. 8 as pad 800.

FIG. 8 is a cross-sectional view of an illustrative embodiment of the pad 660 of the electrode pad 630 of FIG. 6, shown in this FIG. 8 as pad 800. The pad 800 (pad 660 in FIG. 6) comprises a monitoring segment 810 (662 in FIG. 6) and a therapy segment 890 (664 in FIG. 6) which is electrically insulated from the monitoring segment 810 by insulator 880. Signals detected by the monitoring segment 810 are illustratively applied to a monitoring segment lead 661 for transmission toward and beyond monitoring node 652 (in FIG. 6) in accordance with the teachings of FIG. 6. Charge from a defibrillator (601 in FIG. 6) through therapy node 654 (in FIG. 6) are applied to therapy segment lead 663 in FIG. 8 according to the teachings of FIG. 6.

As shown in FIG. 8, the monitoring segment 810 further comprises: a housing 830, an electrode element 840, a gel 850, a spring material 860, a spiked frame 870, and a trigger mechanism 820. The housing 830 receives the electrode element 840 and the gel 850 is received by the housing 830 against the electrode element 840. The spiked frame 870 is received by the housing 830 against the gel 850. The spiked frame 870 defines one or more spikes 872 along a patient facing side 874 of the spiked frame 870. A portion 852 of the gel 850 received by the housing 840 further covers the outwardly facing side 874 of the spiked frame 870. The spring material 860 is disposed between the housing 830 and the spiked frame 870 and connects the housing 830 to the spiked frame 870. The trigger mechanism 820 is connected to the spiked frame 870.

In operation, on activation of the trigger mechanism 820, such as by applying a manual pressure to the top of the trigger mechanism 820, the spiked frame 870 is caused to extend outwardly from the housing 830 against the force of the spring material 860 to cause the one or more spikes 872 to puncture the top layers of the skin of the patient (not shown). On release of the trigger mechanism 820, the one or more spikes 872 are retracted back towards the housing 830 enabling the gel 850 through portion 852 of the gel to provide an electrolytic interface between the punctured skin of the patient and the electrode element 840. The gel 850 then provides a low-impedance path past the stratum corneum, mimi- nizing electrostatically induced artifact, and past the stratum granulosum, minimizing skin stretch artifact. The housing 830 mechanically stabilizes the interface between the electrode element 840 and the gel 850. Stabilizing the interface between the electrode element and the gel is effective in minimizing motion artifact caused by temporary changes in the electrode half-cell potential.

In an alternative embodiment, the spring material 860 may be provided by the insulator 880 which provides the electrical insulating of the therapy segment from the monitoring segment. In one illustrative example of this alternative embodiment, the spring material 860 may be removed and the cavity filled with insulator 880. An alternative example for configuring the insulator 880 to serve and hence replace the spring material 860 is shown and described in FIG. 9. In an alternative embodiment also shown and described in FIG. 9, the spiked frame may be configured for attachment to the housing.

Illustratively, the therapy segment 890 may be in the shape of an annulus having an inside wall that defines a first opening 892 for receiving the insulator 880 which provides the electrical insulating of the therapy segment 890 from the monitoring segment 810. The insulator may also illustratively be in the shape of an annulus having an inside wall that defines a second opening 882 for receiving the monitoring segment 810.

Figure 9:
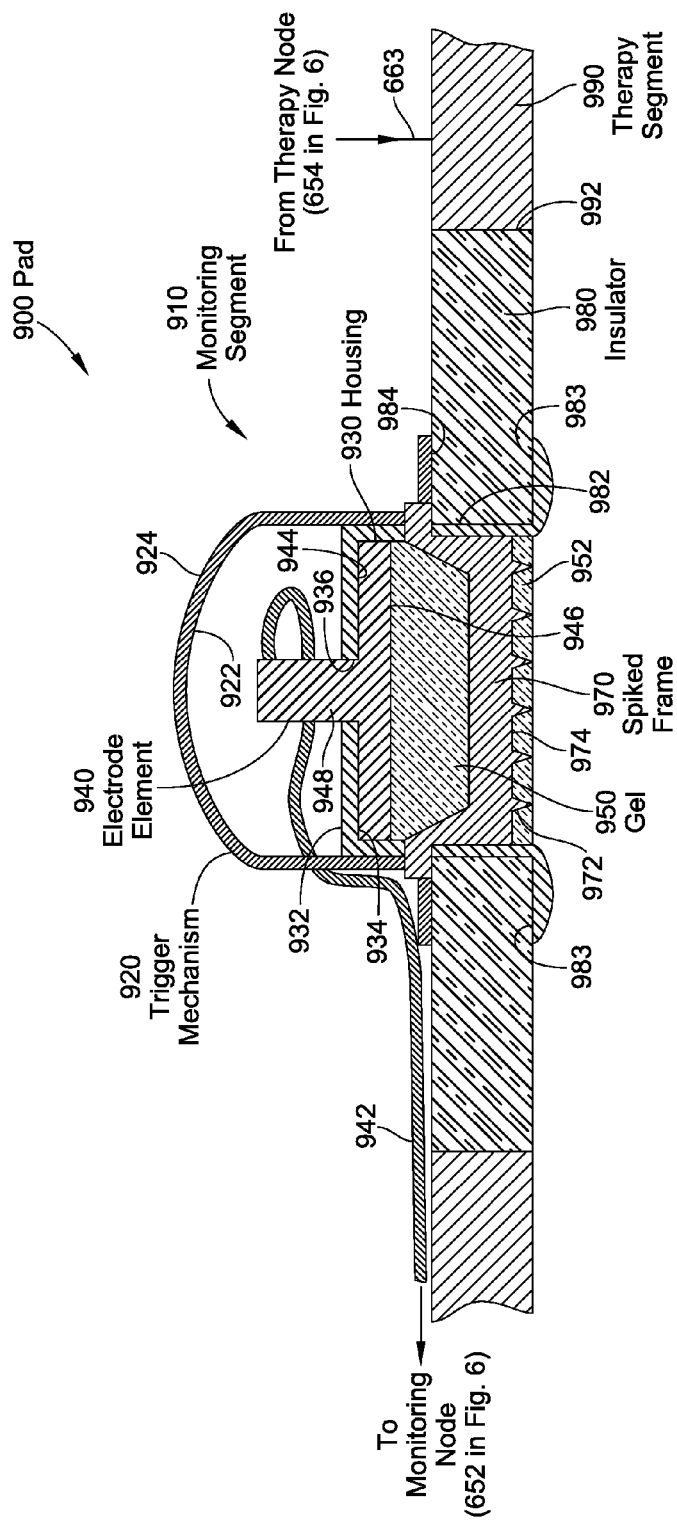
FIG. 9 is a cross-sectional view of an alternative illustrative embodiment of the pad 660 of the electrode pad 630 of FIG. 6, shown in this FIG. 9 as pad 900.

FIG. 9 is a cross-sectional view of an alternative illustrative embodiment of the pad 660 of the electrode pad 630 of FIG. 6, shown in this FIG. 9 as pad 900. The pad 900 (pad 660 in FIG. 6) comprises a monitoring segment 910 (662 in FIG. 6) and a therapy segment 990 (664 in FIG. 6) which is electrically insulated from the monitoring segment 910 by insulator 980. Signals detected by the monitoring segment 910 are illustratively applied to a monitoring segment lead 942 for transmission toward and beyond monitoring node 652 (in FIG. 6) in accordance with the teachings of FIG. 6. Charge from a defibrillator (601 in FIG. 6) through therapy node 654 (in FIG. 6) are applied to therapy segment lead 663 in FIG. 9 according to the teachings of FIG. 6.

As shown in FIG. 9, the monitoring segment 910 further comprises: a housing 930, an electrode element 940, a gel 950, a spiked frame 970, and a trigger mechanism 920. The housing 930 receives the electrode element 940 and the gel 950 is received by the housing 930 against the electrode element 940. The spiked frame 970 is received by the housing 930 against the gel 950. The spiked frame 970 defines one or more spikes 972 along a patient facing side 974 of the spiked frame 970. A portion 952 of the gel 950 received by the housing 930 further covers the outwardly facing side 974 of the spiked frame 972. In FIG. 9, the spring material 860 of FIG. 8 is provided by insulator 980 which also provides a substrate for supporting the interconnection of the trigger mechanism 920 and the spiked frame 970 for concerted movement as well as supporting the interconnection of the housing 930 to the spiked frame 970.

Illustratively, the therapy segment 990 may be in the shape of an annulus having an inside wall that defines a first opening 992 for receiving the insulator 980 which provides the electrical insulating of the therapy segment 990 from the monitoring segment 910. The insulator may also illustratively be in the shape of an annulus having an inside wall that defines a second opening 982 for receiving the monitoring segment 910.

In this example, the trigger mechanism is configured in the shape of a shell including a closed side 922 and an open side 924. The shell is configured for attachment along a first side 984 of the insulator substrate 980. In addition, the housing 930 includes an open side 934 and a closed side 932. The closed side 932 of the housing 930 extends through the second opening 982 of the insulator 980. The housing 930 is configured for attachment along a second side 983 of the insulator substrate 980. The housing defines a third opening 936. The electrode element 940 includes the monitor segment wire lead 942 attached thereto received by the housing 930. The electrode element 940 includes a first side 946 and a second side 944. The second side 944 defines a post 948 for extending through the third opening 936 of the housing 930. The gel 950 is received by the housing 930 against the first side 946 of the electrode element 940. The spiked frame 970 is received by the housing 930 against the gel 950 which is configured for attachment to the insulator substrate 980.

In operation, activation of the trigger mechanism 920 may occur by, for example, applying a manual pressure to the top of the shell that provides the trigger mechanism 920. On activation, the spiked frame 970 is caused to to extend outwardly from the housing 930 against the force of the insulator 980 to cause the one or more spikes 972 to puncture the top layers of the skin of the patient (not shown). On release of the trigger mechanism 920, force applied to the shell is relaxed; enabling both the one or more spikes 972 to retract back into the housing 930 to enable the gel 950 and portion 952 of the gel to provide an electrolytic interface between the punctured skin of the patient and the electrode element 940.

The foregoing description has generally been directed to an illustrative electrode (630 in FIG. 6)—and illustrative embodiments for configuring the pad 660 of that electrode as it is referred to in FIG. 6 (or pad 800 or pad 900 as it is referred to in FIGS. 8 and 9)—for use in monitoring a patient 680 (in FIG. 6) and delivering a charge to the patient in connection with a cardiac arrhythmia according to this disclosure. In one defibrillator system illustrated in FIG. 6, the defibrillator system 600 includes the electrode 630 and the adapter 610 coupled to the defibrillator. This is the defibrillator system 600 in which the other electrode pad 620 and other wire lead 622 are shown in phantom. In another defibrillator system 600, the other electrode pad 620 and other wire lead 622 are included in the defibrillator system 600. In this example, both the electrode pad 630 and the other electrode pad 620 are coupled to one end of the adapter 610 which on the other end is coupled to the defibrillator to provide the defibrillator system 600.

It will be appreciated from the foregoing disclosure that the electrode pad 630 may alone or in combination with the other electrode pad 620 be coupled through the adapter to the defibrillator 601 to control when an electrical charge is applied to a patient and to control the ECG signal that is being received from the patient. We now turn to a discussion of the ways in which the first combination circuit of the electrode 630 of FIG. 6 as shown in FIG. 7 may be configured within the defibrillator system of this disclosure to provide further advantages. For this discussion, we turn to FIGS. 10A-C which show the illustrative circuit of FIG. 7 implemented in three defibrillator system embodiments according to this disclosure.

Figure 10A:
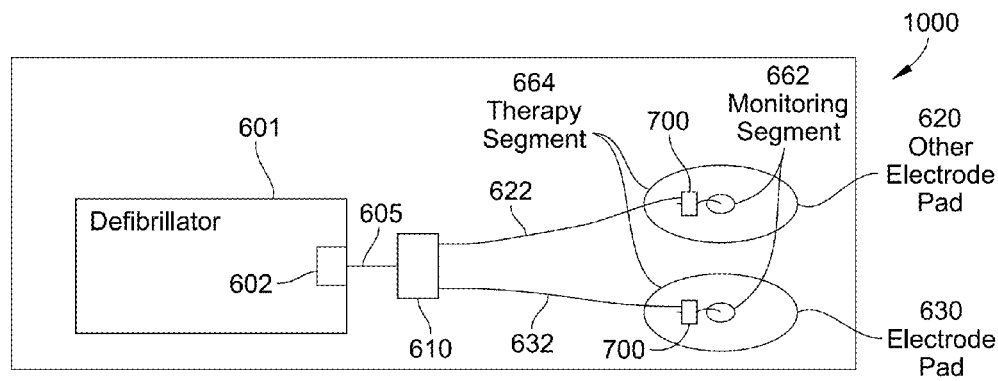
FIGS. 10A-C show the illustrative circuit of FIG. 7 implemented in three defibrillator system embodiments according to this disclosure.
Figure 10B:
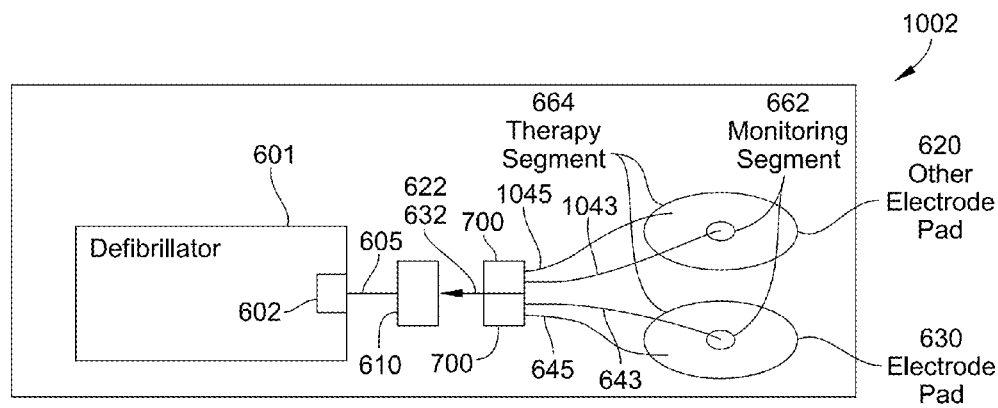
Figure 10C:
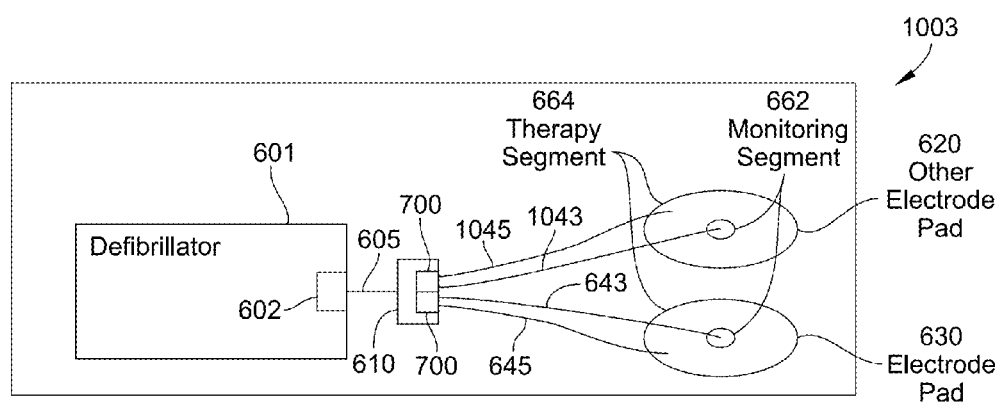

FIG. 10A shows an illustrative defibrillator system 1000, FIG. 10B shows an illustrative defibrillator system 1002, and FIG. 10C shows an illustrative defibrillator system 1003. Each of the defibrillator systems 1000, 1002, and 1003 include a defibrillator 601 including a defibrillation and monitoring port 602, an adapter 610 coupled to the defibrillator 601 via a signal path 605, a FIG. 7 combination circuit, a monitoring segment 662, and a therapy segment 664. The function, configuration, and operation of these components and the FIG. 7 combination circuit have been described in connection with FIGS. 6 and 7 above and these components have the like function, configuration, and operation in the illustrative embodiments shown in FIGS. 10A-C. The signal path 605 is also referred to as a conductor and FIGS. 10A-C show how an adapter may couple the monitoring segment and the therapy segment of one or more pads to a single conductor for connection to the defibrillator.

The differences between the illustrative embodiments shown in FIGS. 10A-C lie in where the FIG. 7 combination circuit is configured in each of the illustrative defibrillator systems. In the defibrillator system 1000 of FIG. 10A, one FIG. 7 combination circuit is illustratively configured to reside on each of the electrode pad 630 and the other electrode pad 620. This is made possible by using a longer lead for each of the wire lead 632 of the electrode pad 630 and the other wire lead 622 of the other electrode pad, respectively, described in FIGS. 6 and 7 in connection with the combination circuit FIG. 7 as shown in FIG. 10A. The longer lead allows the FIG. 7 combination circuit to advantageously be located at the site of the electrode pad 630 and the other electrode pad 620 to reduce the electrical interference between the therapy segment 664 and the monitoring segment 662 as well as ECG artifacts while allowing for easy connection to a remotely located adapter 610. In this embodiment, a separate circuit package is required for each of the respective FIG. 7 combination circuits. There is also a need to bundle or integrate each of the separate circuit packages to each of the electrode pads. The reduction in electrical interference and ECG artifacts at the site of the electrode pad makes the defibrillator system 1000 of FIG. 10A an elegant solution for use with electrode pad designs in which the separate circuit packages may be designed into the pads for increased efficiencies and economies.

In the defibrillator system 1002 of FIG. 10B, the FIG. 7 combination circuit for each of the electrode pad 630 and the other electrode pad 620 have been moved upstream of the electrode pad 630 and the other electrode pad 620 but they still reside downstream of the adapter 610. This is made possible by using a longer lead for each of the monitoring electrode lead 643 and the therapy electrode lead 645 described in FIG. 7 in connection with the FIG. 7 combination circuit as shown in FIG. 10B. FIG. 10B shows the monitoring electrode lead 643 and the therapy electrode lead 645 in connection with the electrode pad 630 but it will be appreciated that like longer monitoring electrode lead and therapy electrode lead are also used for the other electrode pad 620 and they have been shown in FIG. 10B as monitoring electrode lead 1043 and therapy electrode lead 1045. The use of longer therapy electrode leads 645, 1045 and longer monitoring electrode leads 643, 1043 allow the two FIG. 7 combination circuits to be moved away from the electrode pads 620. 630 to avoid any need for bundling of these combination circuits with the electrode pads. The two FIG. 7 combination circuits further reside remotely from the adapter 610, and so avoid any need for bundling with the adapter. The two FIG. 7 combination circuits are coupled to the adapter 610 via wire lead 632 and other wire lead 622 previously described in connection with FIGS. 6 and 7. These create economies and efficiencies. For instance, as a package that is separate from the electrode pads and the adapter, the two FIG. 7 combination circuits may be advantageously bundled together into a single package for further economies and efficiencies. In addition, the separate packaging also allows offloading of the FIG. 7 combination circuit from the electrode pads to enable configuring both monitoring segment and therapy segment residing on each electrode pad of this disclosure to provide further efficiencies and economies.

In the defibrillator system 1003 of FIG. 10C, the FIG. 7 combination circuit for each of the electrode pad 630 and the other electrode pad 620 have been moved upstream of the electrode pad 630 and the other electrode pad 620 and integrated into the adapter 610. The use of longer therapy electrode leads 645, 1045 and longer monitoring electrode leads 643, 1043 allow the two FIG. 7 combination circuits to be moved away from the electrode pads to avoid any need for bundling with the electrode pads which may provide efficiencies and economies as described above. In addition, the two FIG. 7 combination circuits reside in the adapter 610 in this example and so may provide efficiencies and economies through bundling and/or integration of the circuitry that make up the combination circuits and the circuits that make up the adapter 610 into a single package. The two FIG. 7 combination circuits are coupled to the circuitry that makes up the adapter 610 via wire lead 632 and other wire lead 622 (neither are shown in FIG. 10C) as previously described in connection with FIGS. 6 and 7. These create economies and efficiencies. For instance, in addition to the economies and efficiencies from bundling or integrating of the circuitry of the adapter and combination circuit as described above, the FIG. 10C embodiment also allows offloading of the FIG. 7 combination circuit from the electrode pads. This enables configuring both monitoring segment and therapy segment residing on each electrode pad of this disclosure to provide further efficiencies and economies.

Figure 11:
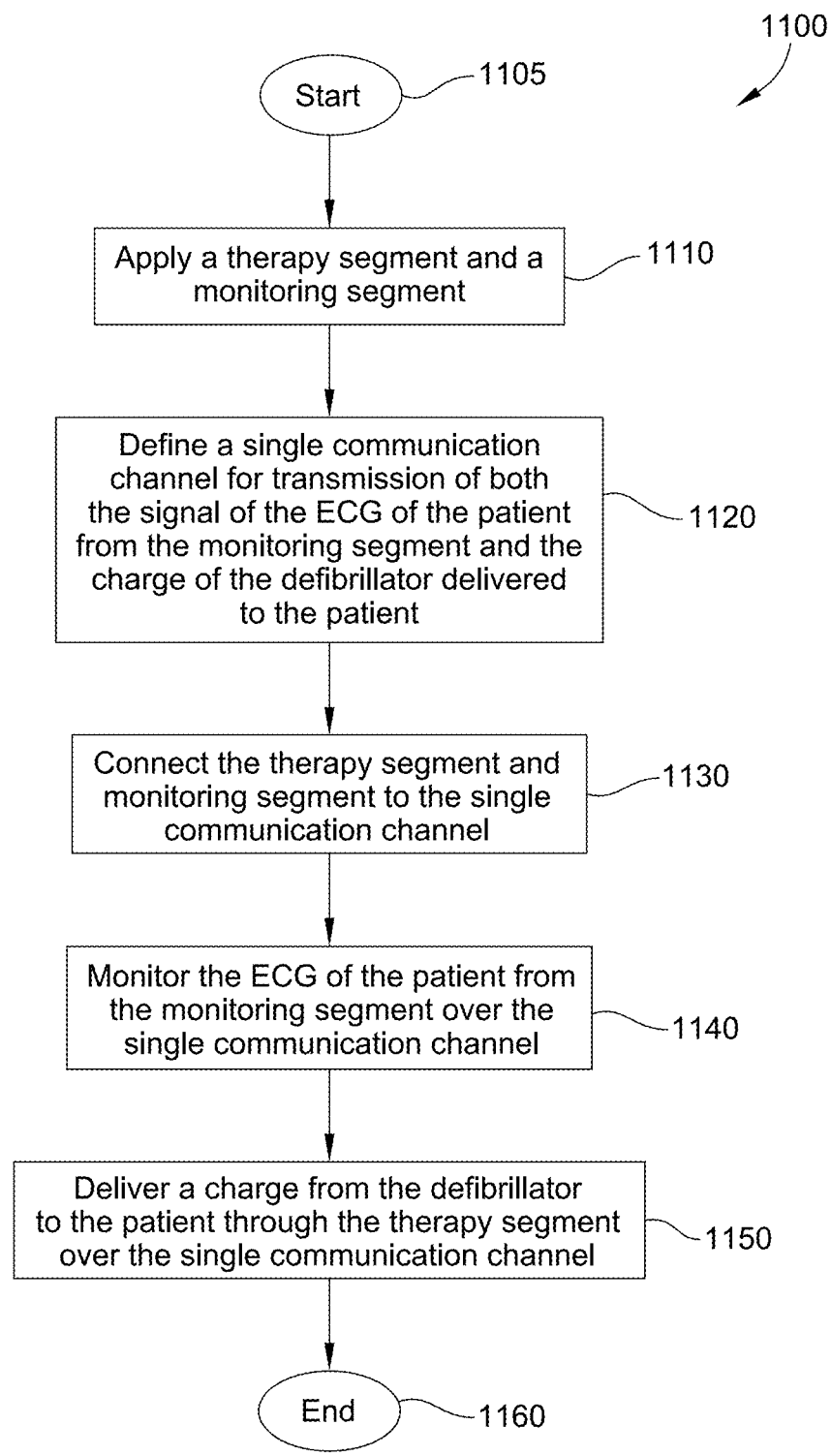
FIG. 11 is an illustrative method for practicing this disclosure.

FIG. 11 is an illustrative method 1100 for monitoring and delivering a charge to a patient by an external defibrillator. The method starts at step 1105. At step 1110, a therapy segment and a monitoring segment is applied to a patient. At step 1120, a single communication channel is defined for transmission of both the signal of an ECG signal of the patient from the monitoring segment and the charge of the defibrillator to the therapy segment for delivery to the patient. At step 1130, the therapy segment and the monitoring segment are connected to a defibrillator through the single communication channel. At step 1140, the ECG signal of the patient from the monitoring segment is monitored over the single communication channel. At step 1150, a charge from the defibrillator is applied to the patient through the therapy segment over the single communication channel. At step 1160 the method ends.

In an alternative embodiment, the step of connect the therapy segment and the monitoring segment to a defibrillator through the single communication channel further comprises the steps of: connect the therapy segment and the monitoring segment to an adapter; and connect the adapter to the defibrillator. In an alternative embodiment, the step of apply the monitoring segment to the patient further comprises the step of: activate a trigger mechanism on the monitoring segment; puncture the skin of the patient in response to the activation of the trigger mechanism; apply a gel to provide an electrolytic interface between the punctured skin of the patient and an electrode element in the monitoring segment. In an alternative embodiment, the monitoring segment comprises: a housing; an electrode element received by the housing; a gel received by the housing against a side of the electrode element; a spiked frame received by the housing against the gel, the spiked frame defining one or more spikes along an outwardly facing side of the spiked frame, the gel received by the housing covering the outwardly facing side of the spiked frame; a spring material disposed between the housing and the spiked frame, the spring material connecting the housing to the spiked frame; the trigger mechanism connected to the spiked frame for causing the spiked frame to extend outwardly from the housing against the force of the spring on activation of the trigger mechanism to cause the one or more spikes to puncture the skin of the patient; and wherein the step of activate the trigger mechanism causes the spiked frame to extend outwardly from the housing against the force of the spring for enabling the step of puncturing the skin; and wherein the step of apply the gel to provide an electrolytic interface between the punctured skin of the patient occurs on releasing the trigger mechanism.

There is thus disclosed an electrode for use with an external defibrillator for a patient. The electrode comprises a first combination circuit. The first combination circuit includes a circuit node electrically coupled to an adapter for coupling to the defibrillator. The circuit node is further coupled to a monitoring node defined by a monitoring segment of a first pad of the electrode and to a therapy node defined by a therapy segment of the first pad of the electrode. The therapy segment is electrically insulated from the monitoring segment. The first combination circuit further includes a capacitor coupled between the circuit node and the therapy node.

In alternative embodiments, the first combination circuit may further comprise a resistor connected between the circuit node and the monitoring node for minimizing the current flow of the charge signal across the resistor; a first diode connected between the circuit node and the therapy node in parallel with the capacitor for passing the flow of the charge generated by the defibrillator for application to the therapy segment in a forward direction; and a second diode connected between the circuit node and the therapy node in parallel with the capacitor for passing the flow of the charge generated by the defibrillator for application to the therapy segment in a reverse direction. The capacitor that is coupled between the circuit node and the therapy node passes the high frequency, low voltage signal generated by the defibrillator for measuring impedance for application to the therapy segment. In a preferred embodiment, the therapy segment will cover a much larger skin area than the monitoring segment, which will result in a much lower impedance (at high frequencies) between the therapy segment and the patient compared to the impedance between the monitoring segment and the patient. Thus, the impedance measured will be that of the lower impedance path through the therapy segment.

The disclosed electrode may be used with a second electrode provided with a second combination circuit that has the same function, configuration and operation as the first combination circuit of the first electrode and is likewise adapted to the adapter. The adapter may be configured to route ECG signals from the monitoring segment of the first electrode or the combination first and second electrode for use by the defibrillator and to route a charge generated by the defibrillator for application to the therapy segment of the first electrode or the combination of first and second electrode. Alternative embodiments of the first electrode and the combination first and second electrodes with adapter coupled to a defibrillator provide alternative defibrillator systems.

While the charge applied to a patient during a defibrillation has been described in this disclosure generally in connection with a defibrillation charge, it will be appreciated that the charge delivered by the therapy segment to the patient from the defibrillator may be a charge for any purpose, including delivering a pacing pulse for controlling the rate of the heartbeat of a patient.

This disclosure provides an electrode including a combination circuit which advantageously reduces the electrical interference between the electrical operation of the monitoring segment and the therapy segments. Advantageously, the combination circuit of the disclosure may reside at the site of the electrode, between the electrode and adapter, or at the site of the adapter, each providing a different set of efficiencies and economies to the electrode for improving the performance of the electrode.

The electrode of this disclosure advantageously provides solutions for reducing ECG artifact during the operation of the electrode, while maintaining the defibrillation, impedance measurement, and ECG acquisition functions of electrodes. For example, the disclosed pads utilize a separate therapy and monitoring segment on each pad thereby isolating the monitoring functionality from the therapy functionality in the operation of the defibrillator. The disclosed pads may further include a mechanism for easy skin preparation after the pads have been applied to the patient. The integration of this skin preparation mechanism with the pads enables skin preparation to be brought to the defibrillation site every time the pads are placed on a patient. Hence, skin preparation is made possible through this disclosure in every defibrillation process thereby minimizing ECG artifact such as resulting from deformation of the electrode's metal-electrolyte interface (which temporarily changes the electrode's half-cell potential), or from movement of electrostatically charged rescuers near the patient or the defibrillator even when the patient is not touched. The disclosure includes electrical components for routing of therapy and monitoring signals that have been independently generated by the separate therapy and monitoring segments of this disclosure. In addition, the disclosed capacitor 644 (FIG. 6) also allows for the high frequency, low voltage signal generated by the defibrillator for measuring impedance to be passed to the therapy node while blocking the lower frequency ECG signal's path from the therapy segment of the electrode.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. For example, while the skin preparation is illustrated as occurring by a penetration of the skin by a spiked frame, it will be appreciated that other mechanisms for penetrating the skin may be used with this disclosure. For example, skin preparation may also be done by abrasion, such as by use of an abrasive dome structure integrated to the pads of this disclosure that rests against the skin and abrades the skin when it is spun. Alternatively, a strip of sandpaper may be attached by adhesion or in other ways to the surface of the monitoring segment that faces the patient. After the monitoring segment is applied to the patient, the strip of sandpaper may be pulled out and discarded. The strip of sandpaper would abrade the skin when removed; leaving the gel to collapse against the abraded skin for reducing electrical and ECG artifact interference. As another example of a modification, each diode in the disclosed embodiments could have one or more additional diodes added in parallel with it, which would potentially improve reliability of the electrode system by providing an alternate current path in case one diode failed and became an open circuit.

Such ways can include equivalents to what is described herein. In addition, the invention may be practiced in combination with other systems. The following claims define certain combinations and subcombinations of elements, features, steps, and/or functions, which are regarded as novel and non-obvious. Additional claims for other combinations and subcombinations may be presented in this or a related document.

We claim:

1. An electrode for use with an external defibrillator for a patient, comprising:
a monitoring segment, the monitoring segment including an electrode element, a skin preparation element configured to prepare the skin of the patient, a gel in contact with the electrode element, and a triggering mechanism; the skin preparation element being movable relative to the electrode element in response to activation of the triggering mechanism.

2. The electrode of claim 1 wherein the skin preparation element is a spiked frame and the gel is on either side of the spiked frame.

3. The electrode of claim 2 further comprising:
a substrate configured to provide a support platform; the monitoring segment being attached to the support platform.

4. The electrode of claim 3 wherein the substrate is an insulator.

5. The electrode of claim 4 further comprising:
a housing; the housing receiving the electrode element.

6. The electrode of claim 5 wherein the housing receives the gel against the electrode element.

7. The electrode of claim 6 wherein the spiked frame is received by the housing against the gel.

8. The electrode of claim 2 wherein the spiked frame defines at least one spike along a patient facing side of the spiked frame.

9. The electrode of claim 3 wherein the substrate comprises an insulator, the electrode further including a therapy segment, the insulator configured to provide electrical insulation between the monitoring segment and the therapy segment.

10. The electrode of claim 9 wherein the therapy segment defines a first opening for receiving the insulator.

11. The electrode of claim 9 wherein the insulator defines a second opening for receiving the monitoring segment.

12. The electrode of claim 5 further comprising:
a monitor segment wire lead;
wherein the electrode element is configured to define a post on one side of the electrode element;
wherein the housing defines a third opening, the post of the electrode extending through the third opening for receiving the post; and
wherein the post is attached to the monitor segment wire.

13. The electrode of claim 4 wherein the trigger mechanism is configured for attachment to the insulator.

14. The electrode of claim 5 further comprising a spring material, the spring material disposed between the housing and the spiked frame, the spring material connecting the housing to the spiked frame, the spiked frame being outwardly movable relative to the electrode element against the force of the spring material in response to the triggering mechanism.

15. The electrode of claim 14 wherein the spiked frame being inwardly movable relative to the electrode element in response to relaxation of the spring material.

16. The electrode of claim 5 wherein the housing mechanically stabilizes the interface between the electrode element and the gel.

17. An electrode for use with an external defibrillator for a patient, comprising:
a housing;
an electrode element received by the housing;
a gel received by the housing and in contact with the electrode element;
a spiked frame, the spiked frame also in contact with the gel, the spiked frame defining one or more spikes along an outwardly facing side of the spiked frame, the gel received by the housing covering the outwardly facing side of the spiked frame;
a spring material disposed between the housing and the spiked frame, the spring material connecting the housing to the spiked frame; and
a trigger mechanism connected to the spiked frame configured for causing the spiked frame to extend outwardly from the housing against force of the spring on activation of the trigger mechanism;
wherein the one or more spikes are adapted to retract back towards the housing on release of the trigger mechanism, enabling the gel to provide an electrolytic interface to the electrode element.

18. A method for monitoring a patient and delivering a charge to a patient by an external defibrillator, the method comprising the steps of:
activating a trigger mechanism;
extending at least one spike outwardly from a monitoring segment in response to activation of the trigger mechanism;
puncturing the skin of the patient with the at least one spike in response to the activation of the trigger mechanism; and
electrolytically interfacing the punctured skin of the patient to an electrode element in response to the trigger mechanism.

19. The method of claim 18 wherein the step of electrolytically interfacing is provided by a gel.

20. A method for manufacturing an electrode for use with an external defibrillator for a patient, comprising the steps of:
defining a post on one side of an electrode element;
defining an opening in a housing;
extending the post of the electrode through the opening;
attaching the post of the electrode to a monitor segment wire;
attaching a spiked frame configured to puncture the skin of the patient to the housing;
providing a gel on either side of the spiked frame and in contact with the electrode element; and
attaching a triggering mechanism to the housing; the spiked frame being movable relative to the electrode element in response to the triggering mechanism.

21. The method of claim 20 further comprising the steps of:
defining an opening in a therapy segment for receiving an insulator; and
defining an opening in the insulator for receiving the housing.

22. The method of claim 21 further comprising the step of:
disposing a spring or material with spring like characteristics between the housing and the spiked frame;
positioning the spiked frame to be in a retracted position with respect to the housing when the spring is in a relaxed state;
positioning the spiked frame to be in an extended position with respect to the housing when the spring is in tension.

* * * * *